United States Patent
Kollgaard et al.

(10) Patent No.: US 10,209,223 B2
(45) Date of Patent: Feb. 19, 2019

(54) REAL-TIME FUSION OF ULTRASOUND AND EDDY CURRENT DATA DURING NON-DESTRUCTIVE EXAMINATION

(71) Applicant: The Boeing Company, Chicago, IL (US)

(72) Inventors: Jeffrey R. Kollgaard, Seattle, WA (US); Tyler M. Holmes, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 756 days.

(21) Appl. No.: 14/721,055

(22) Filed: May 26, 2015

(65) Prior Publication Data

US 2016/0349213 A1    Dec. 1, 2016

(51) Int. Cl.
*G01N 27/90* (2006.01)
*G01N 29/06* (2006.01)
*G01N 29/07* (2006.01)
*G01N 29/11* (2006.01)
*G01N 29/44* (2006.01)

(52) U.S. Cl.
CPC ..... *G01N 27/9073* (2013.01); *G01N 29/0645* (2013.01); *G01N 29/0654* (2013.01); *G01N 29/07* (2013.01); *G01N 29/11* (2013.01); *G01N 29/4436* (2013.01); *G01N 27/904* (2013.01); *G01N 2291/044* (2013.01); *G01N 2291/106* (2013.01)

(58) Field of Classification Search
CPC .. G01N 27/90; G01N 27/9006; G01N 27/902; G01N 27/904; G01N 27/9033; G01N 27/9046; G01N 27/9073; G01N 27/908
See application file for complete search history.

(56) References Cited

U.S. PATENT DOCUMENTS

| | | | | |
|---|---|---|---|---|
| 4,167,878 A | * | 9/1979 | Bottcher | G01N 29/2412 73/601 |
| 4,745,809 A | * | 5/1988 | Collins | G01B 7/105 324/226 |
| 4,814,703 A | * | 3/1989 | Carr | G01B 7/14 324/207.26 |
| 4,856,337 A | * | 8/1989 | Metala | G01N 27/902 324/220 |

(Continued)

*Primary Examiner* — Peter J Macchiarolo
*Assistant Examiner* — Alexander A Mercado
(74) *Attorney, Agent, or Firm* — Ostrager Chong Flaherty & Broitman P.C.

(57) ABSTRACT

Apparatus and methods for real-time fusion of data acquired using ultrasonic and eddy current area sensors during non-destructive examination. The ultrasonic data is acquired using an array of ultrasonic transducer elements configured to enable the production and display of a C-scan of a small area. The ultrasonic transducer array may be one- or two-dimensional. The eddy current sensor can be a single pair of induction coils, a multiplicity of coil pairs, or a coil configuration in which the numbers of drive coils and sense coils are not equal. The eddy current sensor is able to provide data about the test material, such as material thickness or conductivity, to complement the ultrasonic data or enable auto-setup of the ultrasonic inspection device.

5 Claims, 8 Drawing Sheets

(56) References Cited

U.S. PATENT DOCUMENTS

| | | | |
|---|---|---|---|
| 4,955,235 A * | 9/1990 | Metala | G01N 27/902 324/226 |
| 5,062,298 A * | 11/1991 | Falcoff | G01B 7/105 324/229 |
| 5,161,413 A * | 11/1992 | Junker | G01N 29/223 73/634 |
| 5,389,876 A | 2/1995 | Hedengren et al. | |
| 5,418,823 A * | 5/1995 | Kervinen | G01B 7/105 376/245 |
| 5,481,916 A * | 1/1996 | MacEcek | G01N 27/9013 324/226 |
| 5,915,277 A * | 6/1999 | Patton | G01N 27/9033 73/601 |
| 6,914,427 B2 | 7/2005 | Gifford et al. | |
| 7,617,730 B2 | 11/2009 | Georgeson | |
| 7,994,781 B2 | 8/2011 | Goldfine et al. | |
| 8,453,928 B2 | 6/2013 | Melandso et al. | |
| 8,662,395 B2 | 3/2014 | Melandso et al. | |
| 8,704,513 B2 | 4/2014 | Lepage | |
| 2007/0113655 A1* | 5/2007 | Reed | G01N 29/07 73/606 |
| 2007/0126422 A1 | 6/2007 | Crouch et al. | |
| 2008/0309200 A1 | 12/2008 | Melandso et al. | |
| 2009/0139335 A1* | 6/2009 | Kroning | B06B 1/04 73/597 |
| 2010/0097057 A1* | 4/2010 | Karpen | G01N 21/8806 324/238 |

\* cited by examiner

REAL-TIME FUSION OF ULTRASOUND AND EDDY CURRENT DATA DURING NON-DESTRUCTIVE EXAMINATION

BACKGROUND

This disclosure generally relates to apparatus and methods for non-destructive examination (NDE) of structural elements and, more particularly, relates to NDE techniques which combine data acquired using both eddy current and ultrasonic sensors.

In the past, C-scan data fusion was accomplished after the fact by performing sequential scans and then aligning them to the same index points and combining the data. In the case where point measurement eddy current signals were used to supplement ultrasonic measurements, the eddy current measurements were usually taken by sensors adjacent to the ultrasonic transducer, but not located collinearly with the ultrasonic transducer. As a result, the eddy current measurements did not reflect the character of the material being ultrasonically tested immediately below the transducer. In addition to data fusion applications, eddy current data acquired from the same volume of material could be provided as feedback to the ultrasonic device for use in an automated calibration procedure.

It would be desirable to provide improved means and methods for nondestructive examination in which ultrasonic and eddy current area sensors are arranged to interrogate the same volume of material.

SUMMARY

The subject matter disclosed herein is directed to apparatus and methods for real-time fusion of data acquired using ultrasonic and eddy current area sensors during nondestructive examination. The ultrasonic data is acquired using an array of ultrasonic transducer elements configured to enable the production and display of a C-scan of a small area. The ultrasonic transducer array may be a one-dimensional (i.e., linear) array or a two-dimensional (i.e., matrix) array. The eddy current sensor can be a single pair of induction coils, a multiplicity of coil pairs, or a coil configuration in which the numbers of drive coils and sense coils are not equal. Preferably the induction coils are arranged on a flexible substrate placed in the path of the ultrasonic beams transmitted by the ultrasonic transducer array, i.e., between the ultrasonic transducer array and the test material (i.e., workpiece). The eddy current sensor is able to provide data about the test material, such as material thickness or conductivity, to complement the ultrasonic data or enable auto-setup of the ultrasonic inspection device.

The apparatus disclosed in detail below can accomplish data fusion or feedback in real time using collinear ultrasonic and eddy current area sensors that are interrogating the same volume of material. An ultrasonic transducer array is located above an eddy current sensor and essentially transmits through it. Results are acquired in real time and auto-indexed through the collinear arrangement, enabling true data fusion in real time with no need for the cumbersome process of indexing, scaling, and combining separate ultrasonic and eddy current scans after the fact, i.e., during post-processing.

In addition, feedback control becomes possible when the sensors are collinear, so that an ultrasonic device can be calibrated automatically and "on the fly". This may make it possible for less-skilled operators to perform sophisticated inspections. For process control situations, such as automated tape layup, the system can be configured to enable real-time feedback on tow alignment faults, using eddy current and ultrasonic measurements in combination.

One aspect of the subject matter disclosed in detail below is a method for non-destructive examination of a test material, comprising: (a) arranging an eddy current sensor of an eddy current detection system, an array of ultrasonic transducers of an ultrasonic detection system, and a material so that the eddy current sensor is disposed between the array of ultrasonic transducers and a first portion of the material; (b) interrogating the first portion of material using the eddy current sensor; (c) acquiring first eddy current data from eddy currents induced in the eddy current sensor in response to step (b); (d) interrogating the first portion of material using the array of ultrasonic transducers to transmit ultrasound waves through the eddy current sensor; and (e) acquiring first ultrasonic data from ultrasound waves returned to the array of ultrasonic transducers in response step (d). This method may further comprise: (f) moving the eddy current sensor and array of ultrasonic transducers so that the eddy current sensor is disposed between the array of ultrasonic transducers and a second portion of a material; (g) interrogating the second portion of material using the eddy current sensor; (h) acquiring second eddy current data from eddy currents induced in the eddy current sensor in response to step (g); (i) interrogating the second portion of material using the array of ultrasonic transducers to transmit ultrasound waves through the eddy current sensor; and (j) acquiring second ultrasonic data from ultrasound waves returned to the array of ultrasonic transducers in response step (i).

In cases wherein the material comprises a fiber-reinforced plastic laminate containing a layer of conductive material, the method may further comprise: processing the ultrasonic data to determine whether the fiber-reinforced plastic laminate in the first portion of the material has a delamination; and processing the eddy current data to determine whether the layer of conductive material in the first portion of the material has a fault.

In cases wherein the material comprises conductive material, the method may further comprise: processing the ultrasonic data to determine whether the conductive material in the first portion of the material contains corrosion pits, erosion grooves or disbonding; and processing the eddy current data to determine whether the conductive material in the first portion of the material has a crack.

In cases wherein the material comprises a substrate made of conductive material having a coating made of non-conductive material, the method may further comprise: (f) processing the eddy current data to determine a thickness of the coating; and (g) modifying the ultrasonic data based on the coating thickness determined in step (f).

In cases wherein the material comprises a fiber-reinforced plastic laminate containing a layer of resin reinforced by conductive fibers, the method may further comprise: processing the ultrasonic data to identify changes associated with resin richness or starvation; and processing the eddy current data to identify distortions in the conductive fibers.

In some cases wherein the material comprises a substrate made of conductive material, the method may further comprise: (f) processing the eddy current data to determine a thickness of the substrate; and (g) selecting a parameter of the ultrasound waves to be transmitted in step (d), the selection being dependent on the thickness determined in step (f).

In other cases wherein the material comprises a substrate made of conductive material, the method may further comprise: (f) processing the eddy current data to determine a thickness of the substrate; (g) calculating transmission focal laws based on the thickness determined in step (f), the transmission focal laws comprising a pattern of time delays for pulsing the ultrasonic transducer elements; and (h) programming an ultrasonic pulser/receiver unit with the pattern of time delays prior to step (d).

Another aspect of the subject matter disclosed in detail below is an apparatus for non-destructive examination of material, comprising: an array of ultrasonic transducer elements; an ultrasonic pulser/receiver unit electrically connected to the array of ultrasonic transducer elements; an eddy current sensor comprising a flexible substrate made of dielectric material and electrical conductors embedded in the flexible substrate; and an eddy current instrument electrically connected to the electrical conductors of the eddy current sensor, wherein the array of ultrasonic transducer elements and the eddy current sensor are coupled to each other in an overlapping relationship such that ultrasound waves transmitted by the array of ultrasonic transducer elements would propagate through the flexible substrate of the eddy current sensor.

In accordance with some embodiments, the above-described apparatus may further comprise: a control computer in communication with the eddy current instrument and the ultrasonic pulser/receiver unit, wherein the control computer is programmed to correlate eddy current scan data received from the eddy current instrument with ultrasonic scan data received from the ultrasonic pulser/receiver unit; and a display device operatively coupled to the control computer, wherein the control computer is programmed to control the display device to display eddy current scan data received from the eddy current instrument in combination with ultrasonic scan data received from the ultrasonic pulser/receiver unit.

In accordance with other embodiments, the above-described apparatus may further comprise: a processor in communication with the eddy current instrument, the processor being configured to determine focal laws based on eddy current data output by the eddy current instrument; and a control computer in communication with the processor and the ultrasonic pulser/receiver unit, the control computer being configured to determine ultrasonic array element timing to be employed by the ultrasonic pulser/receiver unit based on the focal laws received from the processor.

A further aspect of the disclosed subject matter is a method for non-destructive examination of a material, comprising: (a) arranging an eddy current sensor of an eddy current detection system, an array of ultrasonic transducers of an ultrasonic detection system, and a material so that the eddy current sensor is disposed between the array of ultrasonic transducers and the material; (b) interrogating the material using the eddy current sensor; (c) acquiring eddy current data from eddy currents induced in the eddy current sensor in response to step (b); (d) processing the eddy current data to determine a thickness of the material near an edge of a doubler; (e) calibrating the ultrasonic detection system using the thickness determined in step (d); (f) after the ultrasonic detection system has been calibrated in step (e), interrogating the material near the edge of the doubler using the array of ultrasonic transducers to transmit ultrasound waves through the eddy current sensor; and (g) acquiring ultrasonic data from ultrasound waves returned to the array of ultrasonic transducers in response to step (f), wherein steps (b) and (f) are performed while the eddy current sensor and the array of ultrasonic transducers are in the same respective positions relative to the material. This method may further comprise determining a depth of an interface within the material based on the ultrasonic data acquired in step (g) and the thickness determined in step (d).

Other aspects of apparatus and methods for real-time fusion of NDE data acquired using ultrasonic and eddy current area sensors are disclosed below.

BRIEF DESCRIPTION OF THE DRAWINGS

Reference will hereinafter be made to the drawings in which similar elements in different drawings bear the same reference numerals.

DETAILED DESCRIPTION

Figure 1:
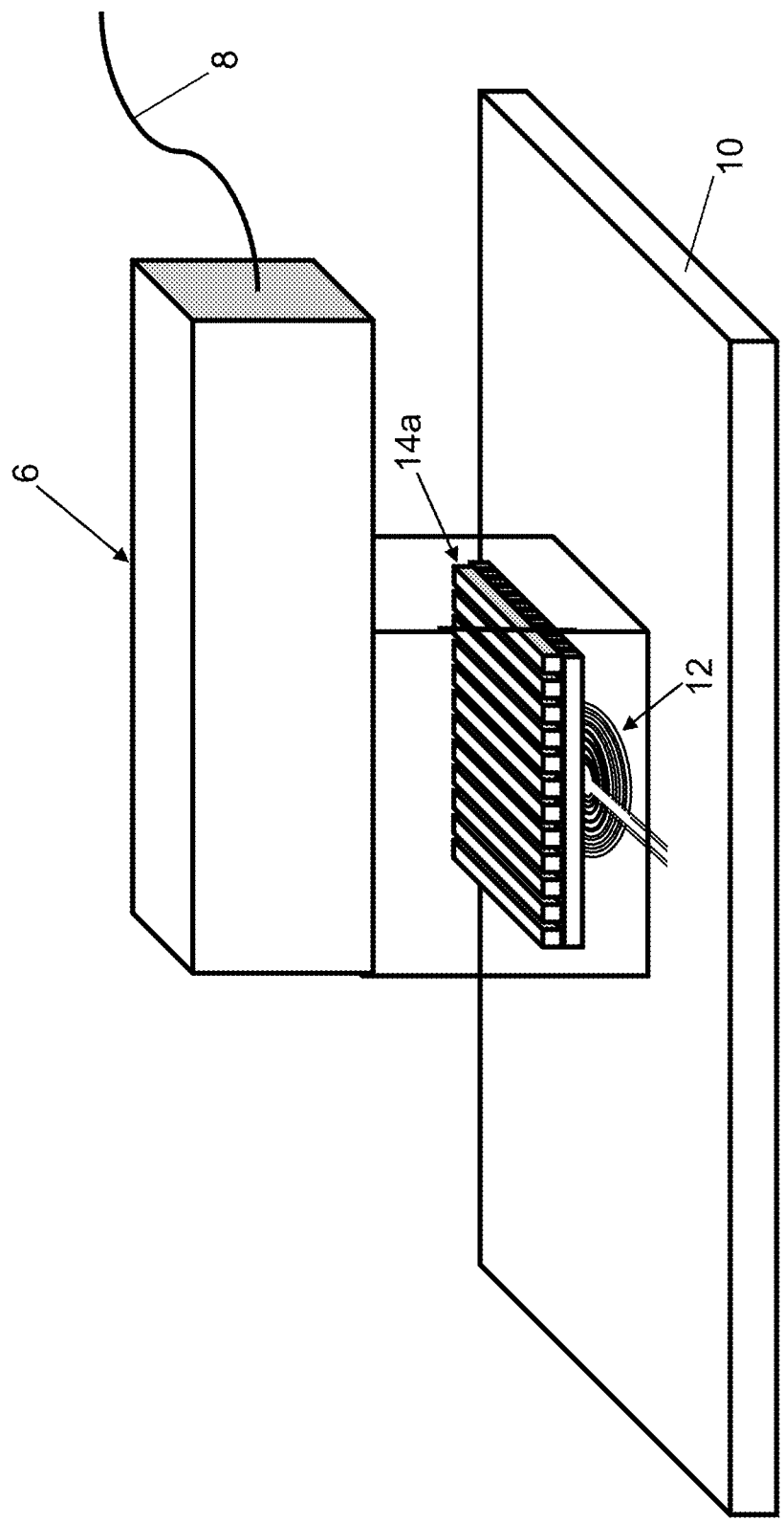
FIG. 1 is a diagram which schematically depicts (in an isometric view) an ultrasonic camera having a two-dimensional array of ultrasonic transducers of a first type overlying and in line with an eddy current sensor that is in contact with a surface of a test material.

Various embodiments will be described for the purpose of illustrating respective applications of the principles summarized above. Some of the embodiments described in detail below can accomplish data fusion and/or feedback in real time using collinear ultrasonic and eddy current area sensors that are interrogating the same volume of material. The ultrasonic transducer array is located above the eddy current sensor and transmits ultrasound waves into and receives ultrasound waves from the test material through the eddy current sensor. As a result, the eddy current measurements reflect the character of the test material being ultrasonically tested immediately below the ultrasonic transducer array.

The ultrasonic data is acquired using an array of ultrasonic transducer elements configured to enable the production and display of a C-scan of a small area. Many different ultrasonic transducer element configurations can be employed. For example, the ultrasonic transducer array may comprise an array of transmit/receive electrodes arranged in rows and columns in a pixel-type configuration. In an alternative configuration, the ultrasonic transducer array comprises a set of mutually parallel elongated transmit electrodes which overlap and cross a set of mutually parallel elongated receive electrodes at a non-zero angle. In still another alternative configuration, the ultrasonic transducer array may be one-dimensional and scanned across a surface to produce the C-scan. The apparatus disclosed herein may employ other types of ultrasonic transducer array.

The eddy current sensor can be a single pair of induction coils, a multiplicity of coil pairs, or a coil configuration in which the numbers of drive coils and sense coils are not equal. Preferably, the coils of the eddy current sensor are printed on a flexible dielectric substrate made from a suitable carrier material, such as biaxially oriented polyethylene terephthalate film. This flexible substrate is placed in the path of the ultrasonic beams transmitted by the ultrasonic transducer array, i.e., between the ultrasonic transducer array and the test material (i.e., workpiece). Such an eddy current sensor would be essentially invisible to the ultrasonic detector and would produce very little interference in the ultrasonic C-scan result. Thus the eddy current sensor is able to provide data about the test material, such as material thickness or conductivity, to complement the ultrasonic data or enable auto-setup of the ultrasonic inspection device.

Eddy current sensors, in many cases, are sensitive to features that ultrasonic sensors cannot detect, such as fatigue cracks or material conductivity. In some cases where a conductive material is part of a carbon fiber laminate, such as a copper foil layer for lightning strike protection, the eddy current sensor can examine the conductive layer for faults while the ultrasonic sensor examines the carbon fiber layer for lightning-induced delamination. There are numerous additional examples of situations where dual-mode data would be useful. Recent aircraft service bulletins, for example, have addressed cracks originating from corrosion pits, chemically milled doubler edge erosion grooves, or disbonded internal doublers that add stress to rivet sites. A dual-mode method could identify the condition causing the cracks and the cracks themselves.

Eddy current sensors are also very sensitive to coating thickness over aluminum structures and can be used to dynamically modify ultrasonic results based on the local coating thickness. Real-time eddy current data can be used to feed back to an ultrasonic device, to optimize calibration and results. Another application would be dynamically calibrated scanning of a multi-thickness metal part with the eddy current results feeding back to the ultrasonic settings to change the focal depth or steering direction of the ultrasonic transducer array (or the transmit frequency) in real time.

Additional applications exist in manufacturing process control. Operations such as automatic tape layup currently require visual inspections to identify layup misalignments and anomalies. Aspects of this invention would enable the examination of tows while providing instantaneous feedback on process deviations, such as tow alignment faults. The eddy current sensors could identify distortions in the conductive fibers while tandem ultrasonic sensors could identify changes associated with resin richness or starvation in the same lengthwise portion of a tow.

FIG. 1 is a diagram which schematically depicts (in an isometric view) portions of a two-dimensional ultrasonic transducer array 14a of a hand-held ultrasonic camera 8 overlying an eddy current sensor 12. The eddy current sensor 12 is placed between an electrically conductive test material 10 and the ultrasonic transducer array 14a. It should be appreciated that eddy current sensor 12 comprises a flexible substrate which is not shown in FIG. 1; only the induction coils of the sensor are depicted. In addition, it should be appreciated that other internal components of the ultrasonic camera 8 are also not shown. The eddy current sensor 12 is preferably mounted directly onto the ultrasonic camera 8. As shown in FIG. 1, the ultrasonic camera 8 can be electrically connected to a computer (not shown) by means of an electrical cable 8. The ultrasonic camera 8 may be a model DolphiCam Expert ultrasonic camera, which is commercially available from DolphiTech AS, Raufoss, Norway.

In the scenario depicted in FIG. 1, the eddy current sensor 12 is lying on and in contact with a surface of the test material 10, while the ultrasonic transducer array 14a overlies and is in line with the eddy current sensor 12. In principle, there can be a medium between the eddy current sensor 12 and the ultrasonic transducer array 14a, as long as the latter can sense structural features/flaws/etc. through the former. For example, the ultrasonic camera 8 may comprise a silicone-based transducer mat (not shown in FIG. 1) that enables dry coupling on painted or shiny surfaces. That transducer mat, although disposed between eddy current sensor 12 and ultrasonic transducer array 14a, would not prevent the passage of ultrasound beams through the eddy current sensor 12. The system can also be used with water or contact gel applied on the surface of the test material 10.

Figure 2:
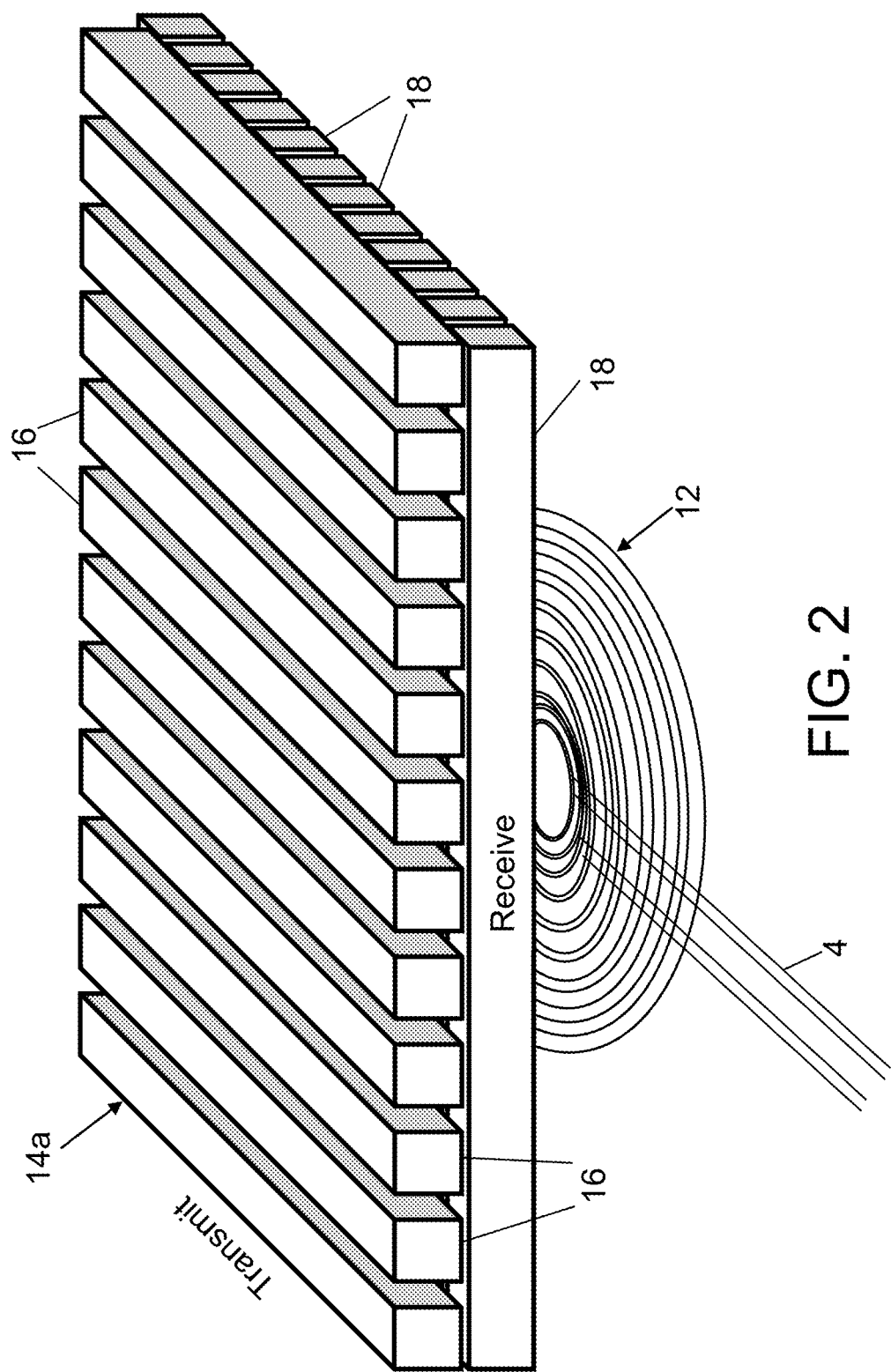
FIG. 2 is a diagram representing an isometric view (on a magnified scale) of the portions of the ultrasonic transducer array and eddy current sensor depicted in FIG. 1.

FIG. 2 shows portions of the ultrasonic transducer array 14a and eddy current sensor 12 on a magnified scale. In accordance with the particular embodiment shown, the eddy current sensor 12 may have circular coils and the ultrasonic transducer array 14a may be of the type disclosed in U.S. Patent Application Publ. No. 2008/0309200 (the disclosure of which is incorporated by reference herein in its entirety). The ultrasonic transducer array comprises one transmitter layer, one receiver layer, and two ground planes. The ground planes are not shown in FIG. 2, while the transmitter and receiver layers are depicted simplistically as comprising a set of mutually parallel elongated transmit elements 16 and a set of mutually parallel elongated receive elements 18 disposed orthogonal to the transmit elements 16. It should be appreciated, however, that the true structure of the transmit and receive layers may be more complicated. For example, the transmit layer, which is depicted in FIG. 2 as being a set of mutually parallel elongated transmit elements 16, may instead comprise a set of mutually parallel elongated transmit electrodes disposed on the upper surface of a first layer of piezoelectric material (e.g., a film made of polyvinylidene fluoride) and a first planar electrode disposed on the lower surface of the first layer of piezoelectric material. Similarly, the receive layer, which is depicted in FIG. 2 as being a set of mutually parallel elongated receive elements 18, may instead comprise a set of mutually parallel elongated receive electrodes disposed on the lower surface of a second layer of piezoelectric material and a second planar electrode disposed on the upper surface of the second layer of piezoelectric material. These transmit and receive layers may in turn be adhered to upper and lower surfaces of a flexible substrate.

Still referring to FIG. 2, the elongated transmit elements 16 overlie and cross over the elongated receive elements 18, thereby providing a matrix of overlapping intersections/pixels which constitute signal points of the ultrasonic transducer array 14a. The elongated electrodes of the transmit elements 16 overlap with the elongated receive elements 18 to form a matrix of individual transducer elements capable of transmitting and receiving ultrasonic waves at their respective locations in the matrix. The transmission and reception of ultrasonic waves must be done in separate operations using multiplexers (not shown) which connect the transmit electrodes to a signal source and connect the receive electrodes to a signal processor. The elongated transmit elements 16 transmit and the elongated receive elements 18 receive alternatingly, the elements in each set incrementing across the matrix. This arrangement uses less processing power and less cabling than an ultrasonic transducer array comprising multiple rows of transducer elements, each row comprising a respective multiplicity of transducer elements (such as the ultrasonic transducer array 14b described below with reference to FIG. 3).

The eddy current sensor 12 shown in FIG. 2 comprises circular induction coils printed on a flexible substrate (not shown). The induction coils are electrically connected to an eddy current instrument (not shown) by means of electrical conductors 4. The induction coils typically comprise at least one drive coil and at least one sense coil. The drive coil is disposed very near the surface of the conductive test material 10 and driven by an alternating current source (not shown in FIG. 2) to create a flux of magnetic field into and below the surface of the conductive test material 10. This flux causes local current to flow in the test material 10. This local current flow induces a mutual magnetic flux of its own. The sense coil operates to receive current mutually induced by the resultant flux due to current flow through the test material 10. Coupling between the coils occurs through the conductive test material itself. Any flaw or defect in the near surface integrity of the test material 10 will disrupt the flow of induced current. This disruption can be detected as a change in voltage detected by the sense coil.

A standard eddy current inspection instrument typically utilizes eddy current sensors made by various manufacturers. Such sensors generally have coil elements operating as drive and sense coils which are disposed in close proximity of one another. The various commercially available eddy current sensors may differ in their winding arrangement and coil connections. Drive coils can typically be configured as individual coils or in a continuous, serpentine line providing uniform, adjacent, parallel segments driven by an external alternating current source. In accordance with alternative embodiments, the eddy current sensor 12 may comprise sensing elements defined by respective sets of parallel elongated inductive coils, which respective sets are disposed at right angles with respect to each other and effectively interact at their points of overlap. An eddy current probe having this type of configuration is disclosed in U.S. Pat. No. 6,914,427, the disclosure of which is incorporated herein in its entirety.

Scanning along the surface of the conductive part being inspected is typically accomplished by moving the eddy current sensor 12 probe across the surface of the test material 10 to cover all regions of interest. The eddy current sensor 12 may take the form of an integrated, microelectronic component coil array comprising a plurality of interconnected, miniaturized eddy current coil elements. More specifically, such arrays can be fabricated within a flexibly conforming structure using precision processing. The integrated component fabrication process provides precision, multi-layer, multi-turn eddy current sensor elements that are substantially identical and their respective electrical connections. An eddy current sensor array may comprise a plurality of small, flexibly interconnected eddy current coil elements to provide a flexible, two-dimensional eddy current sensor which can be placed on a conforming surface to accommodate inspection of irregular conductive surfaces. The coil elements of the plurality are disposed in an array deposited between flexible, multiple fabrication layers being connected therethrough and affixed to a flexible substrate.

Figure 3:
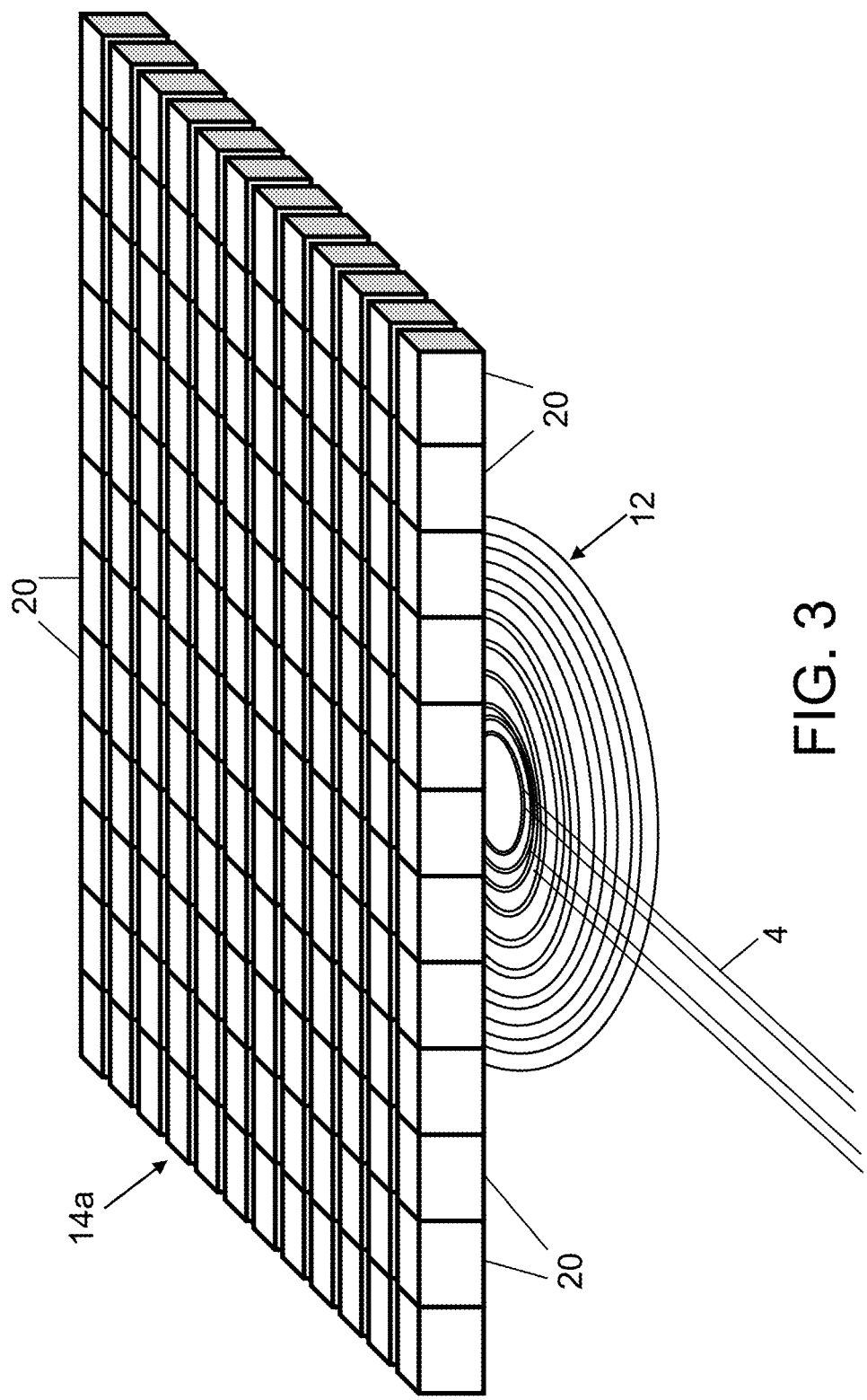
FIG. 3 is a diagram which schematically depicts (in an isometric view) portions of a two-dimensional array of ultrasonic transducers of a second type overlying an eddy current sensor.

FIG. 3 is a diagram which schematically depicts (in an isometric view) portions of a two-dimensional array 14b of ultrasonic transducers of a second type overlying an eddy current sensor 12. In the specific embodiment depicted in FIG. 3, the ultrasonic transducer array 14b comprises a multiplicity of ultrasonic transducer elements 20 arranged in rows and columns to form a 12×12 array. However, the number of transducer elements in each row and the number of transducer elements in each column may be varied. Each ultrasonic transducer element 20 transmits and receives ultrasonic waves. Each ultrasonic transducer element 20 may comprise a layer of piezoelectric material sandwiched between a pair of electrodes. Such an arrangement uses more processing power and more cabling than the ultrasonic transducer array 14a depicted in FIG. 2. The eddy current sensor 12 may be the same as previously described with reference to FIG. 2.

Despite differences in the configurations of the respective ultrasonic transducer arrays 14a and 14b depicted in FIGS. 2 and 3, the resulting apparatuses share the common feature that the ultrasonic transducer elements are located above the eddy current sensor 12 and transmit ultrasound waves into and receive ultrasound waves from the test material 10 through the eddy current sensor 12. As a result, the eddy current measurements reflect the character of the test material being ultrasonically tested immediately below the ultrasonic transducer array.

Figure 4:
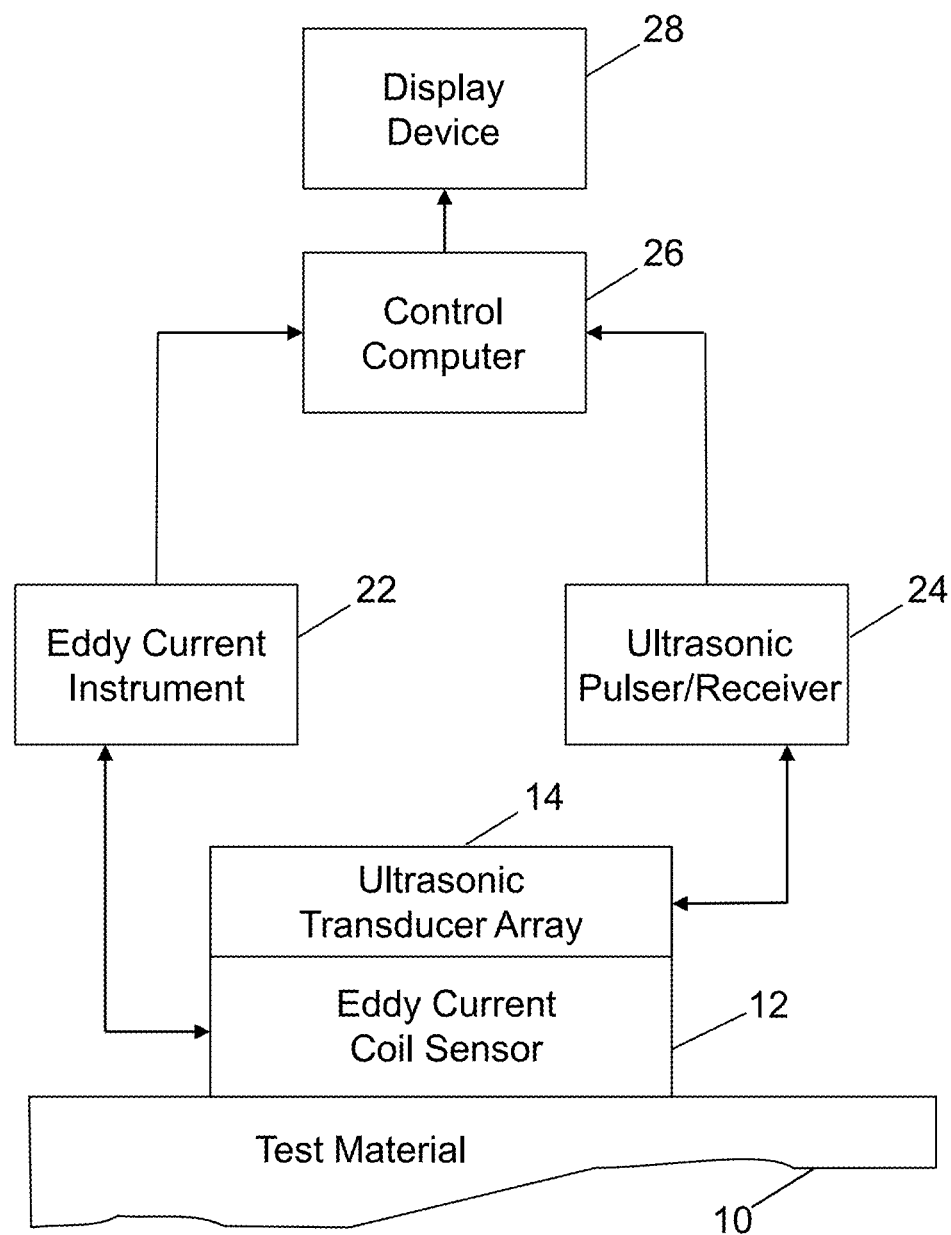
FIG. 4 is a block diagram identifying components of a system for acquiring and displaying fused eddy current and ultrasonic measurement data in accordance with one embodiment.

FIG. 4 is a block diagram identifying components of an apparatus for acquiring and displaying fused eddy current and ultrasonic measurement data in accordance with one embodiment. The system comprises an eddy current sensor 12 in contact with a surface of a test material 10 and an ultrasonic transducer array 14 overlying the eddy current sensor 12. Although FIG. 4 does not show any structure between the ultrasonic transducer array 14 and the eddy current sensor 12, they may be separated by a layer of material that acoustically couples the ultrasonic transducer elements of the array 14 to the eddy current sensor 12. Both the eddy current sensor 12 and the ultrasonic transducer array 14 may be flexible one- or two-dimensional arrays of elements which overlap the same volume of test material.

The apparatus depicted in FIG. 4 comprises an ultrasonic inspection system by which the test material 10, such as an aircraft structure or component, may be inspected. The ultrasonic inspection system includes the ultrasonic transducer array 14, an ultrasonic pulser/receiver unit 24, a control computer 26, and a display device 28. The control computer 26 and display device 28 may be integrated components of a personal computer or a laptop computer. The control computer 26 hosts ultrasonic data acquisition and display software that controls the ultrasonic pulser/receiver unit 24. The control computer 26 may communicate with the ultrasonic pulser/receiver unit 24 via an Ethernet hub (not shown). The ultrasonic pulser/receiver unit 24 is coupled to the ultrasonic transducer array 14. The ultrasonic pulser/receiver unit 24 sends pulses to and receives return signals from the ultrasonic transducer array 14 via an electronics box (not shown). The NDE scan application software running on the control computer 26 controls all details of the scan data and the display of data.

Each ultrasonic transducer element of the ultrasonic transducer array 14 is operable as a pulse-echo inspection sensor that both sends and receives ultrasonic waves. Such sensors are commercially available. The ultrasonic transducer elements can be fabricated from a polymer-based piezoelectric material such as polyvinylidene fluoride. Any number of ultrasonic transducer elements may be arranged in rows and columns with regular spacing to define a square grid pattern. It should be understood that other disposition patterns may be employed, such as hexagonal patterns. In alternative embodiments, the ultrasonic transducer array may have a plurality of ultrasonic transducer elements arranged in a one-dimensional pattern.

The ultrasonic transducer array 14 may be placed in electronic communication with the ultrasonic pulser/receiver unit 24 by way of a cable that can include any number of electrically conductive wires or by way of wireless communication. The ultrasonic pulser/receiver unit 24 generally energizes each ultrasonic transducer element to send an ultrasonic pulse into the test material 10 and then receives an electrical signal generated by the ultrasonic transducer element when an ultrasonic echo signal returns from the test material 10. Ultrasonic pulses traveling through the test material 10 tend to reflect from surfaces, edges, and other discontinuities such as sub-surface defects or interfaces embedded inside the test material 10. A returning ultrasonic echo signal can include multiple time-distributed echo pulses reflected from surfaces and edges that are expected and from damage that deserves investigation and repair. The electrical signal generated by each ultrasonic transducer element conveys amplitude and time data corresponding to the amplitudes and arrival times of echo pulses within the ultrasonic echo signal. The amplitude and time data can be used to discriminate between damage-related echo pulses and echo pulses reflected from undamaged features of a structure. After the ultrasonic pulser/receiver unit 24 energizes one ultrasonic transducer element and collects amplitude and time data therefrom, a brief period of quiescence then passes before the controller energizes another ultrasonic transducer element. By maintaining pulse-echo operations of each ultrasonic transducer element separate in time from operations of each other ultrasonic transducer element, cross-talk among the ultrasonic transducer elements is avoided and the data collected from each ultrasonic transducer element can be associated with each ultrasonic transducer element location. Thus, when the ultrasonic transducer array 14 is disposed against a structure, the data collected from the ultrasonic transducer elements can be associated with localized properties of the structure at the respective ultrasonic transducer element locations.

The control computer 26 receives the collected amplitude and time data from the ultrasonic pulser/receiver unit 24 and graphically displays the data on the display device 28 for interpretation by a user toward identifying damages in the inspected structure. For example, it is well known that the display device 28 may display simulated data from an ultrasonic transducer array 14 having rows and columns of ultrasonic transducer elements. In particular, the display device may display a simulated waveform plot from a particular ultrasonic transducer element in an A-scan window, a simulated cross-section depth image from a column of ultrasonic transducer elements in a vertical B-scan window, a simulated cross-section depth image from a row of ultrasonic transducer elements in a horizontal B-scan window, and a simulated echo-amplitude image taken across a portion of the ultrasonic transducer array 14 in a C-scan window, as seen in U.S. Pat. No. 7,617,730, the disclosure of which is incorporated by reference herein in its entirety.

In accordance with alternative embodiments, the ultrasonic inspection system depicted in FIG. 4 may be programmed with the ability to transmit dynamically focused ultrasound beams which scan the test material by phasing the ultrasonic transducer elements in the ultrasonic transducer array 14 to cover a volume of interest. The phasing is done in accordance with predetermined focal laws. (As used herein, the term "focal laws" refers to the programmed pattern of time delays applied to pulsing and receiving from the individual elements of a transducer array in order to steer and/or focus the resulting ultrasound beam and echo response.) The ultrasonic data analysis application software may select the best return signal for each spatial element of the test material for display as a pixel and discard other return signals.

As seen in FIG. 4, the apparatus further comprises an eddy current sensor 12 disposed between the ultrasonic transducer array 14 and the test material 10. The eddy current sensor 12 is electrically connected to an eddy current instrument 22, which in turn communicates with the control computer 26. The eddy current instrument 22 comprises an eddy current signal processor (not shown), which can be programmed to generate signals representing a property of the test material 10, such as thickness and send those signals to the control computer 26. Thus the apparatus depicted in FIG. 4 has the capability to fuse ultrasonic and eddy current measurement data acquired from the same volume of test material. The eddy current sensor 12 may comprise a multiplicity of induction coils. Each individual induction coil can produce a signal having a phase and amplitude indicative of the sub-surface structure of the test material 10. Multiple analog eddy current signals can be combined into one digital signal using multiplexers. When eddy current array data is multiplexed, the individual eddy current coils are excited at different times, allowing the system to excite all of the coils in the sensor at different times. The signals are then reassembled before being displayed as an image. This data can be referenced to an encoded position and time and represented graphically as a C-scan image, which can be displayed on the display device 28 with the associated ultrasonic C-scan image superimposed thereon (i.e., overlaid).

For example, when inspecting a tube with corrosion loss, the eddy current thickness map could be displayed in gray scale showing wall thickness variations of the tube, while ultrasonic results from a steered or normal beam showing cracks or corrosion could be superimposed in color. The same could be done with coating thickness measured by eddy current using liftoff variation, the coating thickness data being fused with ultrasonic results on the underlying pipe or aircraft landing gear or aircraft fitting. There are a number of variations possible.

Figure 5:
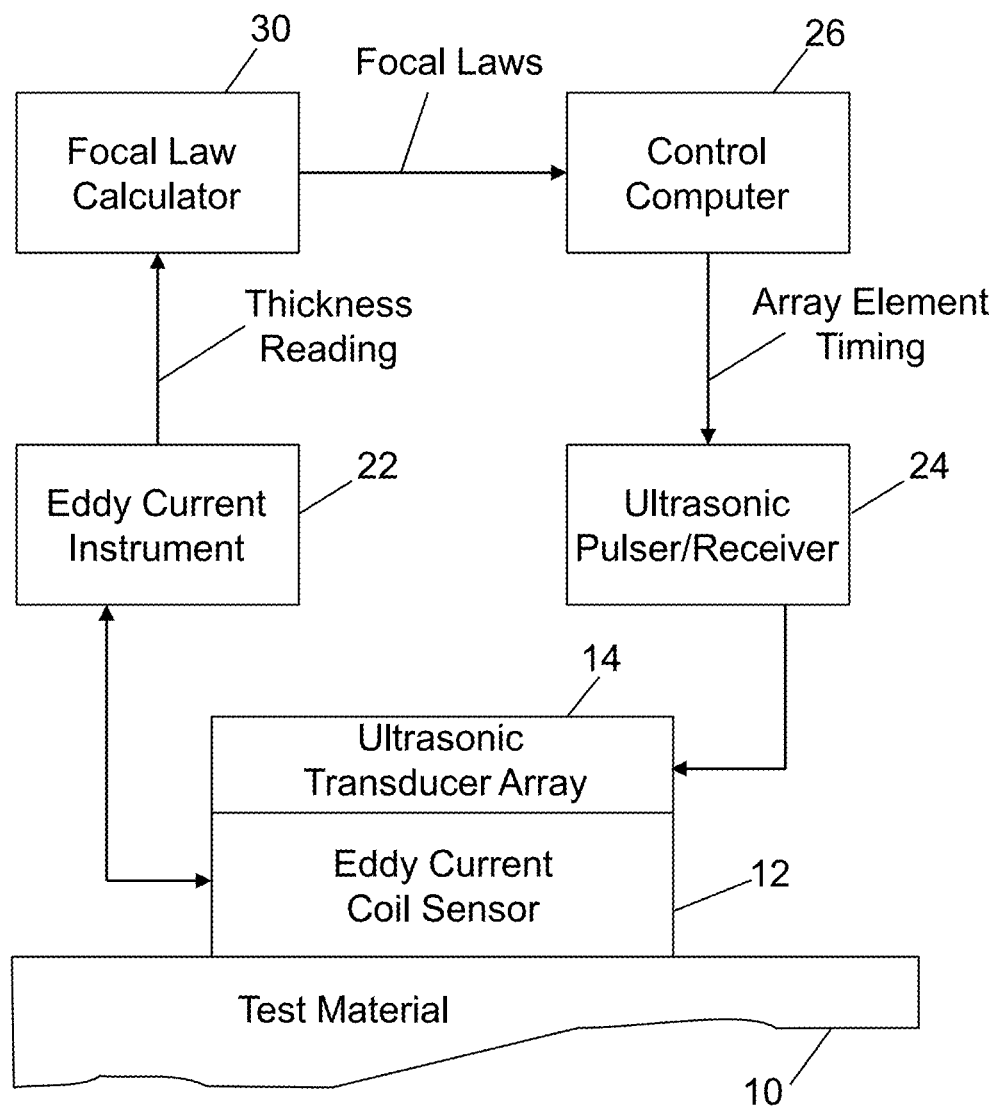
FIG. 5 is a block diagram identifying components of a system for acquiring eddy current measurement data and using that information to dynamically calibrate an ultrasonic inspection device in accordance with another embodiment.

In addition or in the alternative, the eddy current measurement data can be used to dynamically calibrate the ultrasonic inspection system. For example, FIG. 5 is a block diagram identifying components of a system for acquiring eddy current measurement data and using that information to dynamically calibrate the focal laws of an ultrasonic inspection device in accordance with another embodiment. The eddy current signal processor inside the eddy current instrument can be programmed to output a thickness reading to a focal law calculator 30. The focal law calculator may comprise a separate processor programmed to dynamically calculate new focal laws to be adopted by the ultrasonic inspection system in response to changes in the thickness of the test material. The new focal laws would be output to the control computer 26, which computer would be programmed to generate the appropriate array element timing to be used by the ultrasonic pulser/receiver unit 24 during ultrasonic scanning. The eddy current instrument 22 would be calibrated in advance by the technician, in order to output the thickness value that is used by the ultrasonic inspection system for focal law adjustment. In this scenario, the ultrasonic inspection system should be set up so that the focal law setting is a variable dependent on the eddy current sensor output. Other parameters such as ultrasonic frequency, pulse width, and so on would remain fixed. The array element timing can accomplish either focusing of the ultrasonic beam at a particular depth, such as the back surface of the part, to detect things like corrosion pits in a pipeline, or steering of the ultrasonic beam to a particular angle, or sweeping through a range of angles, to intercept cracks that exist on the back side of a part.

Figure 6:
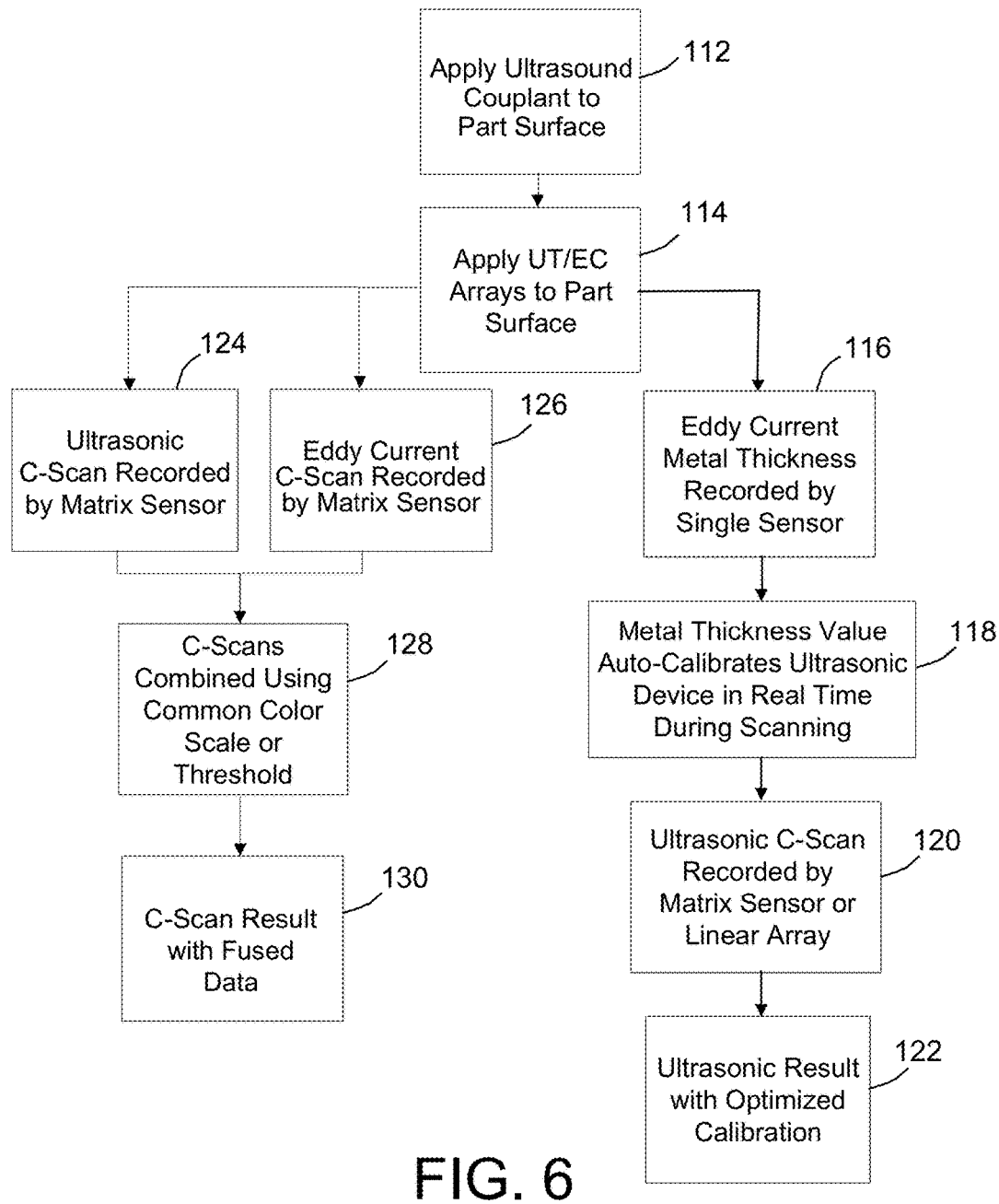
FIG. 6 is a flowchart identifying operations of an NDE process involving both dynamic calibration of an ultrasonic inspection device using eddy current data and fusion of ultrasonic and eddy current data in real time in accordance with one embodiment.

FIG. 6 is a flowchart identifying operations of a first NDE process involving both dynamic calibration of an ultrasonic inspection device using eddy current data and operations of a second NDE process involving real-time fusion of ultrasonic and eddy current data in accordance with one embodiment. As part of the set-up of the apparatus for each of these NDE processes, acoustic couplant can be applied on a surface of the part to be examined (step 112). Then a combined apparatus comprising an ultrasonic transducer (UT) array and an eddy current (EC) sensor are placed on the test material with the eddy current array in contact with the surface of the test material and underneath the ultrasonic transducer array (step 114).

For the dynamic calibration process, the ultrasonic transducer array can be a one-dimensional (i.e., linear) array or a two-dimensional (i.e., matrix) array, while the eddy current sensor may be a one- or two-dimensional array of coil pairs or a single coil pair. In each of these variations, the ultrasonic transducer array and the eddy current sensor may overlap at least partially overlap and have collinear centers. As seen on the right-hand side of FIG. 6, one eddy current coil pair (i.e., "single sensor") can be used during scanning to acquire measurement data and then record the eddy current metal thickness (process 116). The control computer then uses the metal thickness value to auto-calibrate the ultrasonic inspection system in real time during the scanning (process 118). The correctly calibrated ultrasonic inspection system is then used to record ultrasonic C-scan data corresponding to the volume of test material that was scanned. (process 120). The result 122 is ultrasonic C-scan data which more accurately reflects the true state of the test material due to the optimized calibration of the ultrasonic inspection system.

For the data fusion process depicted on the left-hand side of FIG. 6, the ultrasonic transducer array and the eddy current sensor are both matrix arrays which at least partially overlap and have collinear centers. The ultrasonic matrix array is used to record ultrasonic C-scan data (process 124); the eddy current matrix array is used to record eddy current C-scan data (process 126). These processes can be performed in sequence or concurrently. The control computer then combines the ultrasonic and eddy current C-scan data for display on a display device using a common color scale or threshold (process 128). The result 130 is a C-scan image with fused ultrasonic and eddy current data.

Eddy current sensors are helpful for locating subsurface edges in multi-layer metallic assemblies, or second-layer metallic structures buried beneath first layer non-metallic structures. One inspection procedure uses an independent eddy current inspection to locate and mark off subsurface edge sites prone to fatigue cracks, and then follows up with an ultrasonic angle beam phased array inspection.

Figure 7A:
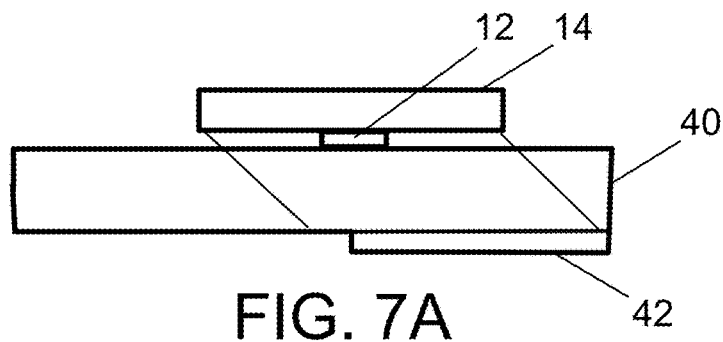
FIGS. 7A through 7D are diagrams showing respective scenarios in which an eddy current sensor and an ultrasonic transducer array are used to detect edges, edges with cracks, edges with erosion, and edges with both cracks and erosion, respectively.
Figure 7B:
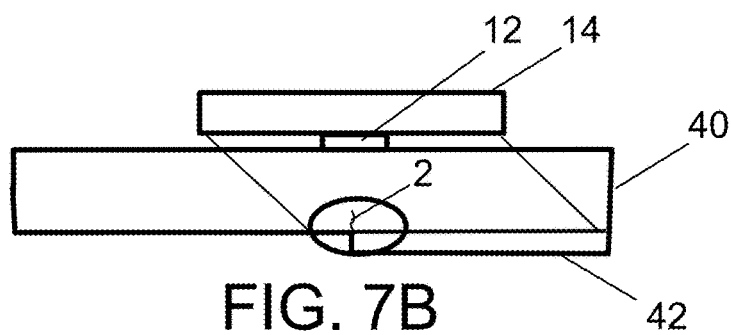

FIGS. 7A and 7B are diagrams showing a scenario in which first an eddy current sensor 12 is used to locate an edge of a chem-mill (i.e., chemically milled) doubler 42 attached to a fuselage skin panel 40 and then a phased ultrasonic transducer array 14 is used to inspect the subsurface site adjacent that edge. The eddy current sensor 12 detects edge and depth. Based on the output of the eddy current sensor 12, focal law parameters are determined and sent to the ultrasonic inspection device. The elements of the ultrasonic transducer array 14 are then controlled to steer an ultrasound beam into the fuselage skin panel 40 at an angle. FIG. 7A shows a situation wherein no crack is present near the edge of the chem-mill doubler 42; FIG. 7B shows a situation wherein a crack 2 is present near the edge of the chem-mill doubler 42.

Figure 7C:
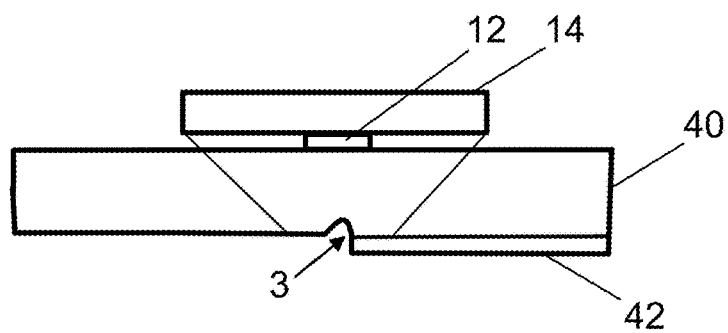

FIG. 7C is a diagram showing a scenario in which first an eddy current sensor 12 is used to locate an edge of a chem-mill doubler 42 attached to a fuselage skin panel 40 and then a phased ultrasonic transducer array 14 is used to inspect the subsurface site adjacent that edge. The eddy current sensor 12 detects edge and depth. Based on the output of the eddy current sensor 12, focal law parameters are determined and sent to the ultrasonic inspection device. The elements of the ultrasonic transducer array 14 are then controlled to focus an ultrasound beam at the detected depth in the fuselage skin panel 40. FIG. 7C shows a situation wherein erosion 3 is present near the edge of the chem-mill doubler 42.

Figure 7D:
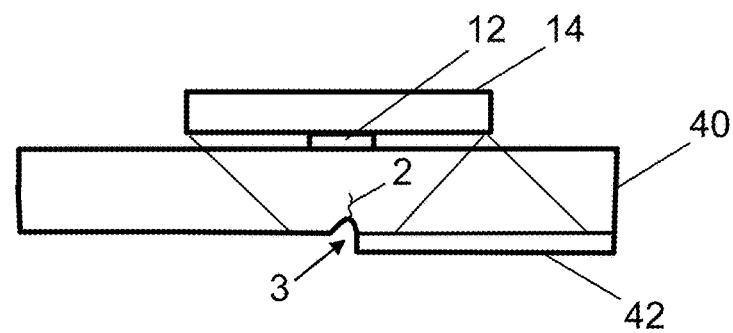

FIG. 7D is a diagram showing a scenario in which two sets of focal law parameters are determined based on the eddy current sensor output and sent to the ultrasonic inspection device. The elements of the ultrasonic transducer array 14 are first controlled to steer an ultrasound beam into the fuselage skin panel 40 at an angle and subsequently controlled to focus an ultrasound beam at the detected depth. FIG. 7D shows a situation wherein both a crack 2 and erosion 3 are present near the edge of the chem-mill doubler 42.

As previously mentioned, additional applications of the data fusion technique disclosed herein exist in manufacturing process control. Ultrasonic and eddy current data fusion would enable the examination of tows during automated tape layup while providing instantaneous feedback on process deviations, such as tow alignment faults. The eddy current sensors could identify distortions in the conductive fibers while tandem ultrasonic sensors could identify changes associated with resin richness or starvation in the same lengthwise portion of a tow. This could be accomplished using pulse echo ultrasonic scanning, in which an ultrasonic transducer array would be disposed on one side of the tow and would both send and receive ultrasound waves. Alternatively, a through-transmission technique could be used.

Figure 8:
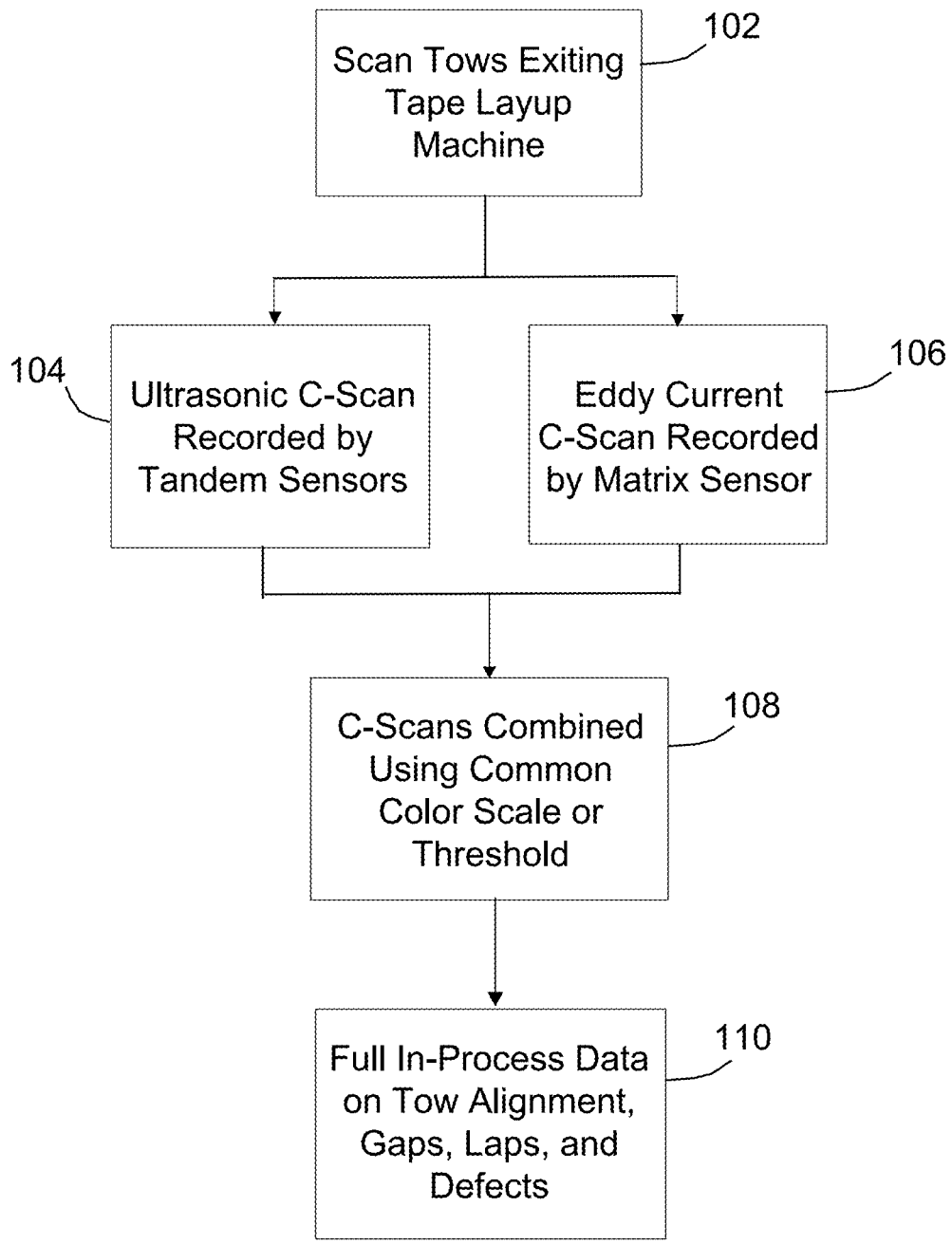
FIG. 8 is a flowchart identifying operations of an in-process inspection of fiber-reinforced plastic material using tandem ultrasonic sensors and an eddy current sensor in accordance with a further embodiment.

FIG. 8 is a flowchart identifying operations of an in-process inspection of fiber-reinforced plastic material that combines eddy current sensing with through-transmission ultrasonic scanning. Tows of fiber-reinforced plastic material are scanned (process 102) using ultrasonic and eddy current sensors. These sensors would operate concurrently. In a preferred configuration, tandem ultrasonic matrix arrays would be disposed on opposite sides of the tow. In one implementation, an eddy current matrix array could be placed on one side of the tow, attached to either the transmitting or the receiving ultrasonic matrix array. In an alternative implementation, a pair of eddy current matrix arrays could be placed on opposite sides of the tow, one attached to the transmitting ultrasonic matrix and the other attached to the receiving ultrasonic matrix array. In either case, the receiving ultrasonic matrix array would record the ultrasonic C-scan data (process 104), while the sensing eddy current matrix array would record the eddy current C-scan data (process 106). The control computer then combines the ultrasonic and eddy current C-scan data for display on a display device using a common color scale or threshold (process 108). The result 110 is full in-process data on tow alignment, gaps, laps, and defects which can be fed back to the control computer to enable real-time process control.

While apparatus and processes for real-time fusion of ultrasonic and eddy current data and real-time feedback of eddy current data to an ultrasonic inspection device (e.g., for dynamic calibration) have been described with reference to various embodiments, it will be understood by those skilled in the art that various changes may be made and equivalents may be substituted for elements thereof without departing from the scope of the claims set forth hereinafter. In addition, many modifications may be made to adapt the teachings herein to a particular situation without departing from the scope of the claims.

The method claims set forth hereinafter should not be construed to require that the steps recited therein be performed in alphabetical order or in the order in which they are recited. Nor should they be construed to exclude any portions of two or more steps being performed concurrently or alternatingly.

The invention claimed is:

1. An apparatus for examination of material, comprising:
   an array of ultrasonic transducer elements;
   an ultrasonic pulser/receiver unit electrically connected to said array of ultrasonic transducer elements;
   an eddy current sensor;
   an eddy current instrument electrically connected to said eddy current sensor, wherein said array of ultrasonic transducer elements and said eddy current sensor are coupled to each other in an overlapping relationship such that ultrasound waves transmitted by said array of ultrasonic transducer elements would propagate through said eddy current sensor;
   a processor in communication with said eddy current instrument, said processor being configured to determine focal laws based on eddy current data output by said eddy current instrument; and
   a control computer in communication with said processor and said ultrasonic pulser/receiver unit, said control computer being configured to determine ultrasonic array element timing to be employed by said ultrasonic pulser/receiver unit based on the focal laws received from said processor.

2. The apparatus as recited in claim 1, wherein said array of ultrasonic transducer elements comprises a multiplicity of ultrasonic transducer elements arranged in rows and columns.

3. The apparatus as recited in claim 1, wherein said array of ultrasonic transducer elements comprises a plurality of mutually parallel transmit electrodes and a plurality of mutually parallel receive electrodes which overlap with, but are not parallel to, said transmit electrodes.

4. The apparatus as recited in claim 1, further comprising a control computer in communication with said eddy current instrument and said ultrasonic pulser/receiver unit, wherein said control computer is programmed to correlate eddy current scan data received from said eddy current instrument with ultrasonic scan data received from said ultrasonic pulser/receiver unit.

5. The apparatus as recited in claim 4, further comprising a display device operatively coupled to said control computer, wherein said control computer is programmed to control said display device to display eddy current scan data received from said eddy current instrument in combination with ultrasonic scan data received from said ultrasonic pulser/receiver unit.

* * * * *